(12) United States Patent
Gaynes

(10) Patent No.: US 7,527,613 B2
(45) Date of Patent: May 5, 2009

(54) THERAPEUTIC SOLUTION DROP DISPENSER

(75) Inventor: Bruce I. Gaynes, Skokie, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 11/696,543

(22) Filed: Apr. 4, 2007

(65) Prior Publication Data
US 2007/0262096 A1 Nov. 15, 2007

Related U.S. Application Data

(60) Provisional application No. 60/789,502, filed on Apr. 5, 2006.

(51) Int. Cl.
*A61M 35/00* (2006.01)
(52) U.S. Cl. .................................. 604/295
(58) Field of Classification Search .......... 604/294–302
See application file for complete search history.

(56) References Cited

U.S. PATENT DOCUMENTS

| 3,998,348 | A | * | 12/1976 | Sammaritano | 215/11.3 |
|---|---|---|---|---|---|
| 4,002,168 | A | | 1/1977 | Petterson | |
| 4,973,322 | A | | 11/1990 | Jewart, Ronald D. | |
| 5,176,654 | A | | 1/1993 | Schreiber | |
| 5,334,172 | A | | 8/1994 | Kelley | |
| 5,382,243 | A | | 1/1995 | Mulholland | |
| 5,611,788 | A | | 3/1997 | Marchment | |
| 5,848,999 | A | | 12/1998 | Basilice et al. | |
| 6,090,086 | A | | 7/2000 | Bolden | |
| 6,423,040 | B1 | * | 7/2002 | Benktzon et al. | 604/300 |
| 6,752,793 | B1 | | 6/2004 | Dascanio et al. | |
| 6,875,201 | B1 | * | 4/2005 | Kawashima et al. | 604/295 |
| 2002/0153386 | A1 | | 10/2002 | Uetake et al. | |
| 2004/0207803 | A1 | | 10/2004 | Paukovits, Jr. | |
| 2004/0267214 | A1 | | 12/2004 | Kerssies | |

OTHER PUBLICATIONS

Mishima, S., "Clinical pharmacokinetics of the eye," *Invest. Opthalmol. Vis. Sci.*, vol. 21, No. 4, Oct. 1981, pp. 504-541; published by Assoc. for Res. In Vis. And Opthal., Inc.

(Continued)

*Primary Examiner*—Manuel A Mendez
(74) *Attorney, Agent, or Firm*—Foley & Lardner LLP

(57) ABSTRACT

Drop dispensers are provided which comprise a first portion, the first portion including a dispensing tip, the dispensing tip including an annular groove around an outer part of the dispensing tip, and a nozzle having a through-opening; and a second portion having a closed end, wherein the first portion is angularly disposed from the second portion and the dispensing tip is distal from the closed end. Exemplary drop dispensers also provide for a removable cannula tip for conveying liquids contained within the drop dispenser to a precise location in the eye, ear, nose, or mouth. Removable cannula tips are provided comprising an aperture for dispensing liquids, and an elastomeric annular ring capable of seating in the annular groove of the dispensing tip, wherein the aperture is distal to the elastomeric annular ring. The drop dispensers described are particularly well suited for the dispensing of ophthalmic solutions.

19 Claims, 3 Drawing Sheets

OTHER PUBLICATIONS

Mills, A. et al., "Development of novel thermochromic plastic films for optical temperature sensing," *Analyst*, vol. 124, 1999, pp. 685-689.

Van Santvliet, L. et al., "Therapeutic Reviews: Determinants of Eye Drop Size" *Surv. Ophthalmol.*, vol. 49, No. 2, Mar.-Apr. 2004, pp. 197-213, (Joel Mindel, Editor); published by Elsevier Inc.

Gaynes, B. I. et al., "Impact of Administration Angle on the Cost of Artificial Tear Solutions: Does Bottle Positioning Minimize Wastage?," *Journal of Ocular Pharmacology and Therapeutics*, vol. 23, No. 2, 2007, pp. 196-201; published by Mary Ann Liebert, Inc.

International Search Report and Written Opinion for PCT/US2007/65974, mailed Jan. 28, 2008.

\* cited by examiner

THERAPEUTIC SOLUTION DROP DISPENSER

FIELD OF THE INVENTION

The invention relates to drop dispensers in general, and more specifically to those for dispensing small amounts of liquids to the eyes, ears, or mouth of a subject. The drop dispensers described are particularly well suited for dispensing ophthalmic solutions.

BACKGROUND

Dispensers of therapeutic solutions to the eye, ear canal, nose, or mouth are well known in the art. In particular, drop dispensers that dispense solutions to a certain part of the eye, in different amounts, or with associated apparatuses for various purposes have been described. In the typical design, a person desiring to put a solution into their own eye is required to tip their head back, pull one or both of their eyelids back, center the dropper over the eye and squeeze out a drop of solution. Some designs have an arm for bracing a bottle, or dispenser, on the cheek, just under the eye, while other designs have elaborate trusses for centering the bottle over the eye, while holding the eyelids back. However, despite the plethora of options available, many dispensers still require the person to assume an uncomfortable position not conducive to using a mirror to aid in the administration, or in the process of administering a solution, they either blink or miss the eye completely, spilling the solution or requiring additional applications. This can be a wasteful process, especially considering the fact that many therapeutic solutions for the eye or ear tend to be quite expensive and may have to be refilled by a pharmacist.

Improper administration of a therapeutic solution by a patient may also account for waste of sometimes expensive ophthalmic pharmaceutical agents, despite explicit administration instructions from a clinician or provider. One such example is eye drops to treat glaucoma. Some glaucoma treatments require patients to administer medicated eye drops, which lower the eye pressure to prevent optic nerve damage and loss of vision. Yet, despite instruction on proper eye drop dispensation and placement, more than one-half of glaucoma patients incorrectly administer drop medication. One factor of improper administration is the dispensing of too little or too much drug per indicated single drop.

Too much or too little drug per drop from a drop dispenser can be caused by the angle of administration. For example, a 45° angle of administration of a drop from a traditional drop dispenser delivers a drop of a different volume than that compared to the same dispenser when held at a 90° angle to the eye. Such differences have been determined using densitometry methods. These methods determine the amount of solution dispensed from a drop dispenser by mass determination and conversion to drop volume based on density. Such drop size differences have been assessed for a wide range of products such as prostanoid analogues Xalatan®, Lumigan® and Travatan® with a once-daily recommended dosage. Difference in drop size between 45° and 90° administration angles were statistically significant for both Travatan and Lumigan (Mann-Whitney, $p<0.001$), however Travatan demonstrated a substantial higher level of discrepancy. The amount of drug delivered by a Travatan bottle increases approximately 16% when administered at a 90° angle vs. a 45° angle to the eye. Such variation in the angle of administration of topical ophthalmic therapy for conditions such as glaucoma can have a significant effect not only in the amount of drug delivered to the eye, but in regard to the costs of medication as well. Gaynes, B. I. and Singa, R. M., unpublished results and also Gaynes, B. I.; Singa, R. M., Schaab, G., and Sorokin, Y., *J. Ocular Pharmacology and Therapeutics* 23(2), 196-201 (2007). Other drop size determinants have been addressed by Santvliet, L. V. et al. *Survey of Ophthamology* 49, 197-213 (2004).

Variation in drop size can also have an impact on overall effectiveness of the drug. For example, too small of a drop to the eye will not result in the desired treatment, however if too large a drop is dispensed the eye cannot absorb all of the drug and excess drug will be expelled during the blinking process or excess tear formation will dilute the drug. Any one of these results can affect the treatment outcome and may lead to wasteful use of sometimes expensive pharmaceutical solutions.

A need exists for drop dispensers that are easy to use and allow a person to self-apply a drop of a therapeutic solution to their own eye in a comfortable manner and in a correct dosage amount.

SUMMARY

The present invention provides generally for a drop dispenser of therapeutic solutions, particularly to the eye, ear, nose, or mouth. In particular, some embodiments allow for a person to dispense a drop of an ophthalmic solution into their own eye, while keeping their head in a normal position, and looking into a mirror to assist in the application.

In one embodiment, a drop dispenser comprises a first portion having a dispensing tip for dispensing fluids, such as a therapeutic or ophthalmic solution, and a second portion having a closed end; wherein the first portion and the second portion are angularly disposed from one another through an angle, $\theta$. In another embodiment, an overall shape of the drop dispenser is a conical shape. In some embodiments, the dispensing tip has a nozzle, with a through-opening such that fluids may flow from the drop dispenser and out the nozzle when pressure is applied to the drop dispenser. The dispensing tip may also have an annular groove for receiving and mating with an elastomeric annular ring of a removable cannula tip comprising an aperture distal to the elastomeric annular ring. In some embodiments, the removable cannula tip allows for precise drop formation, and precise placement of the drop from the drop dispenser into a specific area such as a conjunctival sac. The removable cannula tip may be a one-use item that is replaced each time to allow for multiple uses of the drop dispenser without worry of contamination.

Methods for using an exemplary drop dispenser are also provided in which a subject using the drop dispenser can keep their face vertically positioned in relation to the floor so that a mirror may be easily used to assist the person in application of the therapeutic solution to the desired area.

DETAILED DESCRIPTION

In one aspect, drop dispensers suitable for the dispensation of therapeutic solutions, particularly to the eye, ear, nose, or mouth, are described. Some drop dispensers comprise a first portion having a dispensing tip for dispensing fluids, such as a therapeutic or ophthalmic solution, and a second portion having a closed end; wherein the first portion and the second portion are angularly disposed from one another through an angle, θ. The drop dispenser may also have a removable cannula tip that allows for precise drop formation, and precise placement of the drop from the drop dispenser into a specific area such as a conjunctival sac. The drop dispensers allow for a person to dispense a drop of an ophthalmic solution into their own eye, while keeping their head in a normal position, and looking into a mirror to assist in the application. The drop dispensers, while well-suited to a large range of applications for eye drop dispensation, are particularly well-suited for the dispensation of expensive pharmaceuticals by minimizing droplet waste and the ability to use "every last drop" of solution.

Figure 1:
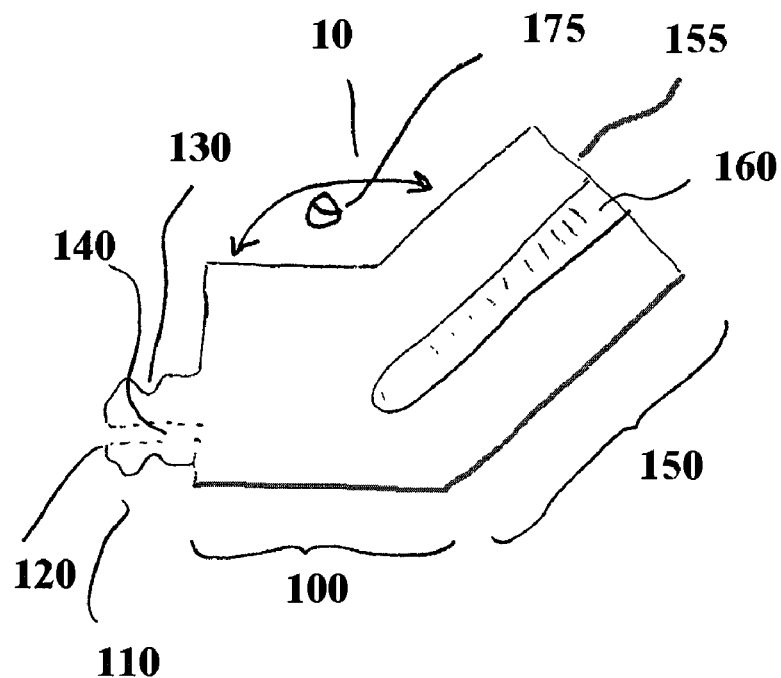
FIG. 1 is a side-view cut-out representation of an exemplary drop dispenser.
Figure 2:
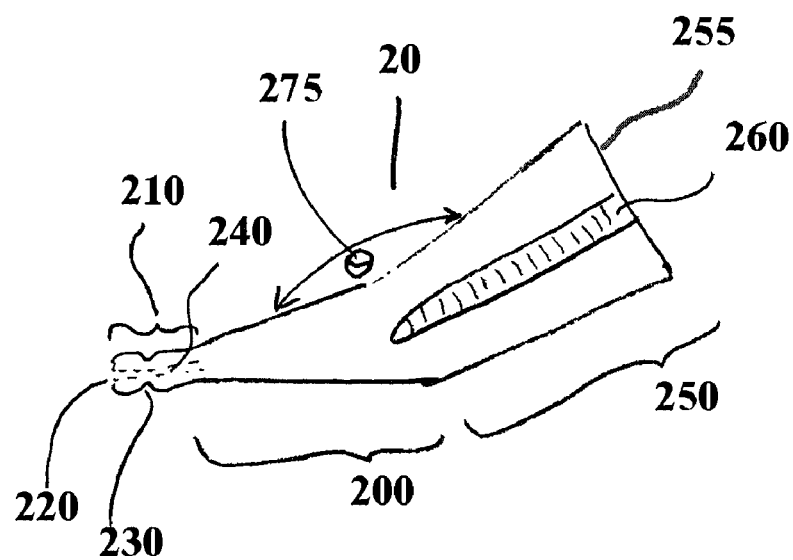
FIG. 2 is a side-view cut-out representation of an exemplary drop dispenser.

FIGS. 1 and 2 are illustrations of exemplary drop dispensers 10, 20 comprising a first portion 100, 200 having a dispensing tip 110, 210 for dispensing fluids and a second portion 150, 250 having a closed end 155, 255; wherein the first portion 100, 200 and the second portion 150, 250 are angularly disposed from one another through an angle 175, 275, represented by θ. The angular disposition 175, 275, is from about 90° to about 180° in some embodiments, or from about 135° to about 178° in other embodiments. In some embodiments, the angular disposition 175, 275, may be such that the drop dispenser 10, 20 may be stood upon the closed end 155, 255 for storage of the drop dispenser 10, 20 on a shelf, without tipping over.

As illustrated in FIG. 2, in order to more easily facilitate use of "every last drop" of a solution that may be contained within the drop dispenser 20, the first portion 200 and the second portion 250 may be cone-shaped, such that an overall shape of the drop dispenser 20 is conical from the closed end 255 to the dispensing tip 210, with a widest end being the closed end 255. In another embodiment, only the first portion is cone-shaped, similar to first portion 210 in FIG. 2, with the first portion being narrower at an end distal to the second portion, than at an end proximal to the second portion, where the second portion is similar to the second portion 150 in FIG. 1. In yet another embodiment, only the second portion is cone-shaped, similar to second portion 250 in FIG. 2, with the second portion narrower at an end proximal to the first portion than at the closed end, where the first portion is similar to the first portion 100 in FIG. 1.

Figure 3:
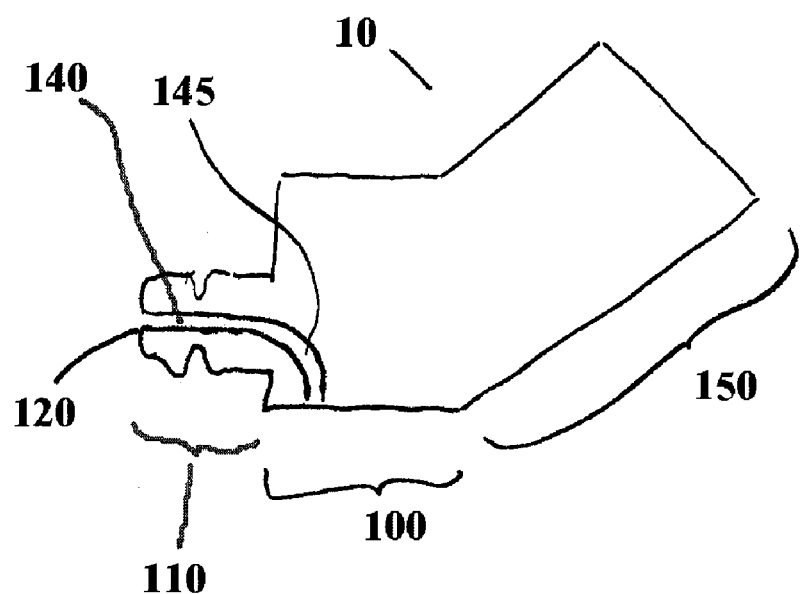
FIG. 3 is a side-view cut-out representation of an exemplary drop dispenser with a dip tube.

In some embodiments, dispensing tips 110, 210, 410 (see FIGS. 1, 2, and 4) include a nozzle 120, 220, 420 having a through-opening 140, 240, 440, such that fluids may flow from the drop dispenser 10, 20 and out the nozzle 120, 220, 420 when pressure is applied to the drop dispenser. The through-opening 140, 240, 440 is long enough to traverse the thickness of the material forming the dispensing tip 110, 210, 410 in some embodiments, and in other embodiments, the through-opening 140, 240, 440 further comprises a tube extending from the nozzle 120, 220, 420 and into the dispensing tip 110, 210, 410. As exemplified in FIG. 3, the through-opening 140 may further comprise a dip tube 145, that extends from the nozzle 120 into the first portion 100, and is curved such that the dip tube 145 is capable of conveying liquids from the lowest point of the drop dispenser 10 when the drop dispenser 10 is held in a dispensing position. Dispensing position refers to the drop dispenser 10, 20 being held a fashion such that the first portion 100, 200 is relatively horizontal and the second portion 150, 250 is disposed at an upward angle. Other positions can also be used for dispensing. The dispensing tip 110, 210, 410 also comprises an annular groove 130, 230, 430 for receiving and mating with an elastomeric annular ring 510, 610 of a removable cannula tip 50, 60 (See FIGS. 5 and 6, described vide infra). In an embodiment such as that illustrated in FIG. 1, the dispensing tip 110 is desirably positioned on the first portion 100 such that when the first portion 100 is held in a dispensing position, the therapeutic solution can easily reach the dispensing tip 110. The position of the dispensing tip 110 on the first portion 100 is such that a shoulder 125 is of a minimal size, and allows for liquid contents of the drop dispenser 10 to easily find the through-opening 140 of the dispensing tip 110, especially when there is little solution left in the drop dispenser 10.

In one embodiment, described drop dispensers are used for the self-application of a therapeutic solution to a subject's own eye without tipping back of the head. Therefore, the first portion of the drop dispenser is to be held in a dispensing position, relatively horizontal, such that the person may look into a mirror for assistance in applying a drop of solution from the drop dispenser. However, in doing so, the person may hold it, for many reasons (i.e. out of habit, comfort, to get the last of the solution further into the tip, etc.), at some angle other than perfectly horizontal. While the first portion of the drop dispenser may be used in a perfectly horizontal position, it is not a requirement that one do so, and when the drop dispenser is held relatively horizontal, relatively horizontal may therefore have a large diversion from perfectly horizontal.

Figure 4:
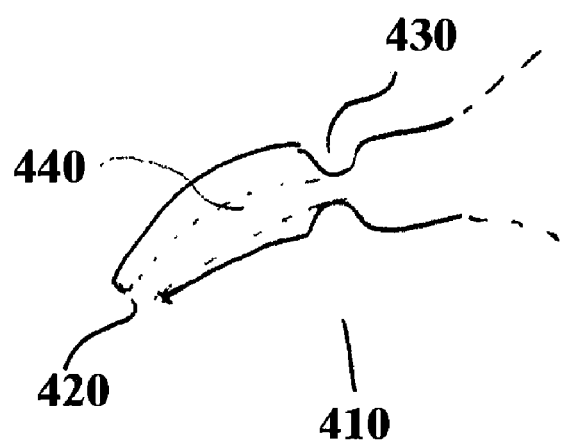
FIG. 4 is a side-view cut-out representation of an exemplary curved dispensing tip.

Drop dispensers can also include a curved dispensing tip 410. FIG. 4 shows one embodiment of the curved dispensing tip 410, with the nozzle 420 being pointed in a downward direction when a drop dispenser, to which the curved dispensing tip 410 is attached, is held in a dispensing position.

Figure 5:
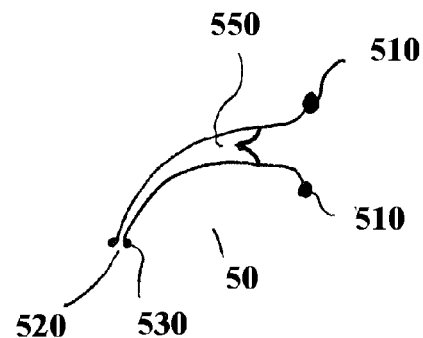
FIG. 5 is a side-view cut-out representation of an exemplary curved, removable cannula tip.
Figure 6:
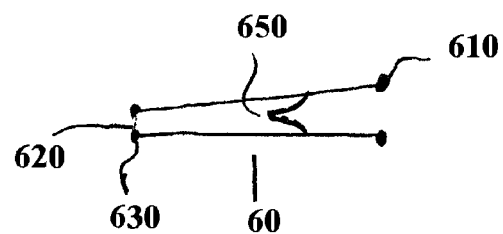
FIG. 6 is a side-view cut-out representation of an exemplary straight, removable cannula tip.

Referring to FIGS. 5 and 6, removable cannula tips 50, 60 serve as a delivery point for liquids that are expelled from the drop dispenser 10, 20, when pressure is applied to the drop dispenser 10, 20. In some embodiments, the removable cannula tip 50 is curved, as illustrated in FIG. 5, and in other embodiments the removable cannula tip 60 is straight, as illustrated in FIG. 6. In general, removable cannula tips 50, 60 comprise an aperture 520, 620 for dispensing liquids, distal to an elastomeric annular ring 510, 610 capable of seating in the annular groove 130, 230, 430 of the dispensing tip 110, 210, 410. The elastomeric annular ring 510, 610 may be made of an elastomeric material that allows for a tight seal between the elastomeric annular ring 510, 610 and the annular groove 130, 230, 430 of the dispensing tip 110, 210, 410. In an optional embodiment, the aperture 520, 620 has a rounded edge 530, 630.

In some embodiments, the removable cannula tip 50, 60 has a unidirectional valve 550, 650. The unidirectional valve 550, 650 is normally closed, but opens as a result of therapeutic solution being forced out through the nozzle 120, 220, 420, into the removable cannula tip 50, 60, and into the unidirectional valve 550, 650 when pressure is applied to the drop dispenser 10, 20. The unidirectional valve 550, 650 is provided to prevent contamination of the contents of the drop dispenser 10, 20, which are normally sterile when introduced to the drop dispenser 10, 20. The unidirectional valve 550, 650 prevents aspiration of other fluids into the drop dispenser 10, 20, if the aperture 520, 620 should come into contact with other fluids or contaminating materials. The removable cannula tip 50, 60 may be replaced after each use to prevent contamination between eyes of a subject or between subjects.

In some embodiments, curved removable cannula tips 50 are used with straight dispensing tips 110, 210. In other embodiments, straight removable cannula tips 60 are used with curved dispensing tips 410, and in such an embodiment, the straight removable cannula tip 60 is forced into a curved orientation by the curved dispensing tip 410.

As shown in FIGS. 1 and 2, a transparent or translucent window 160, 260 may be incorporated into the drop dispenser 10, 20 for viewing the amount of contents remaining. The transparent or translucent window 160, 260 may contain graduation marks through which the user may gauge the usage rate and the amount of contents remaining in the drop dispenser 10, 20. In embodiments where the drop dispenser 10, 20 is made of a transparent or translucent material, the transparent or translucent window 160, 260 is not necessary, however graduation marks may be furnished.

Figure 7:
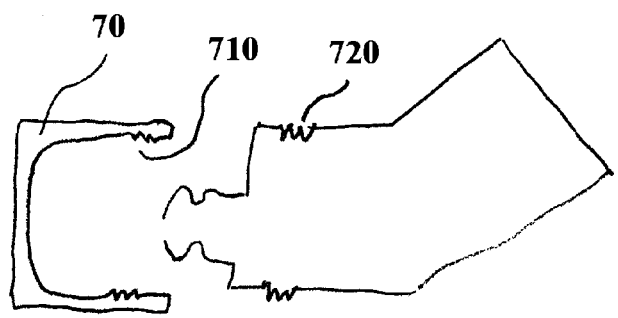
FIG. 7 is a side-view cut-out representation of an exemplary cap and a drop dispenser.

As shown in FIG. 7, a cap 70 can be provided that is used to cover the dispensing tip of a drop dispenser, when the drop dispenser is not in use. In one embodiment, the cap 70 has threads 710 on an inner surface. In such an embodiment, the drop dispenser may have corresponding threads 720 for securing the cap 70 on the drop dispenser. Other embodiments for attaching the cap 70 to the drop dispenser will be readily envisioned by one of skill in the art, and include but are not limited to those in which a cap is press-fit onto the drop dispenser, a cap is hinged onto the drop dispenser, or a cap is clipped onto the drop dispenser via an annular groove or bump on the drop dispenser and a complementary annular bump or groove on the cap.

The exemplary drop dispensers described herein may be constructed of any of a number of polymeric materials. Polymeric materials compatible with the present embodiments may include, but are not limited to, thermoelastic polymers, polyethylene such as low- and hi-density polyethylene or blends thereof, polypropylenes, polyvinylchloride, polycarbonates, polyarylates, polyethylene terephthalate, silicones, mixtures of two or more thereof, and other polymeric materials that are compatible with the solutions to be contained within the drop dispenser. In some embodiments, the polymeric material is low density polyethylene. In other embodiments, the polymeric material is polypropylene. Polymeric materials used to construct drop dispensers may also comprise additives such as stabilizers, plasticizers, lubricants, antioxidants, or a mixture of any two or more thereof. The materials used to construct the drop dispenser should be robust enough for repeated deformation through squeezing, and yet supple enough that squeezing of the drop dispenser may be performed. The drop dispenser may be opaque, translucent, or transparent, however in cases where the drop dispenser is opaque, a transparent or translucent window may be incorporated for easy determination of the amount of solution remaining in the drop dispenser at any given time. The drop dispensers typically are thin-walled containers having a thickness of from about 0.40 mm to about 1.50 mm in some embodiments, from about 0.5 mm to about 1.40 mm in other embodiments, from about 0.6 mm to about 1.30 mm in other embodiments, or from about 0.7 mm to about 1.20 mm in yet other embodiments.

Removable cannula tips described herein may be constructed of any of a number of materials. Those materials include thermoelastic polymers, polyethylenes, polypropylenes, silicones, polyvinylchloride, polycarbonates, polyarylates, polyethylene terephthalate, natural and synthetic rubbers, polymeric mixtures thereof, and other polymeric materials that are both compatible with the solutions to be transferred via the removable cannula tip and non-irritating to eyes, ears, mouths, or skin. Removable cannula tip are preferably constructed of a soft, flexible material. In some embodiments, the soft, flexible material, is a soft elastomeric material with a modulus of elasticity of such that it will not cause damage to the eye or ocular adnexa.

The size of the drop dispensers described herein may also be varied. The size may be altered to correspond to a particular application, size of a prescription, or other determining factor. For example, a prescription for an ophthalmic or other therapeutic solution may be written for only a few uses, in which case the size of the drop dispenser is such that only a few milliliters, or less, are contained within it, or the prescription may be written for a long period of time or for multiple uses, in which case the size of the drop dispenser is such that several milliliters, tens of milliliters, hundreds of milliliters, or more are contained. For example, the drop dispenser may contain from about 0.1 mL to about 250 mL in one aspect, from 0.1 mL to about 100 mL in another aspect, from about 0.1 mL to about 25 mL in another aspect, and from about 0.1 mL to about 5 mL in yet another aspect. The size of the drop dispenser may also be commensurate with non-prescription uses. In addition to sizing being commensurate to a particular application, the size of the drop dispenser should be appropriate for comfortable handling by the user, particularly when the user is the person requiring the application of the solution. Dimensions of the drop dispenser may be dictated by the amount of solution to be contained within the drop dispenser, the desired shape, comfort of the user, or other aesthetic considerations.

Drop volumes from drop dispenser are controlled for a variety of reasons known to those of skill in the art. For example, Mishima has described the pharmacokinetics of eye drops when instilled in an eye, and describes desirable drop ranges to maximize intraocular drug penetration. Mishima, S. *Investigative Opthalmology and Visual Science* 21, 504-541 (1981). In some cases, it is desirable that the size of the drop from the drop dispenser be carefully controlled so as to minimize waste, especially where the pharmaceutical ingredient is particularly expensive.

In some embodiments, the size of a drop dispensed from the apertures may be carefully controlled by the dimensions of the removable cannula tips. Studies have shown that drop sizes in excess of 15 to 20 μL (microliters) may lead to conjunctival irritation and, in some cases, excessive reflex tearing resulting in a dilution of the applied therapeutic solution. Apertures may be from about 0.01 mm to about 3 mm in some embodiments, from about 0.1 mm to about 2 mm in other embodiments, and from about 0.1 mm to about 1.75 mm in yet other embodiments. Droplet sizes produced by the drop dispensers described herein and removable cannula tips described herein are from about 1 μL to about 50 μL in some embodiments, from about 5 μL to about 30 μL in other embodiments, and from about 10 μL to about 25 μL in yet other embodiments.

The drop dispensers are not limited to the dispensation of a particular type of ophthalmic solution. While the drop dispensers may be used to minimize the waste of expensive pharmaceuticals, they may also be used for every day uses such as for artificial tears, or contact lens wetting solutions. Exemplary ophthalmic solutions include, but are not limited to antibiotics, anti-viral agents, anti-inflammatories, anti-histamines, mast-cell stabilizers, lubricants, tear replacements, mydriatics/cyclopleges, and ocular hypotensives. The drop dispenser may be used to deliver the pharmaceuticals where the systemic drug absorption of topical ophthalmic drugs occurs directly through the nasal vasculature and is therefore similar to intramuscular or intravenous injection. Thus the drop dispenser may be used to for the administration of biologic materials such as insulin or immunomodulators such as interferon or monoclonal antibodies. The ability to easily change the dose, by changing the removable cannula tip, is a desirable feature for the delivery of any of the above pharmaceutical or biological materials, or solutions.

Methods of using the described drop dispensers are also provided. As noted above, one of the problems plaguing other drop dispenser designs, especially those intended for delivery of a therapeutic solution to the eye, is that the person requiring the solution must tip their head back so that the drop falls into the eye. Exemplary drop dispensers eliminate that requirement by allowing the person to keep their head in a substantially vertical position, while looking in a mirror to assist in the application of the solution. In one embodiment, such a method of using the drop dispenser comprises providing a subject in need of an eye treatment with an ophthalmic solution contained within the drop dispenser; holding the drop dispenser in a dispensing position, such that a face of the subject remains relatively vertical, the first portion of the drop dispenser is relatively horizontal and the second portion of the drop dispenser is positioned in an upward angle; bringing the aperture of the removable cannula tip into close proximity with an eye; and squeezing the drop dispenser to expel a drop of the ophthalmic solution from the drop dispenser, through the removable cannula tip, out of the aperture, and onto the eye. In another embodiment, the eye comprises a conjunctival sac (i.e. a space between the lower eyelid and the eye) and the drop is expelled into the conjunctival sac.

In other embodiments of methods for using described drop dispensers, the person applying the drop to an affected area may not be the person with an eye affliction. In such an embodiment, the person with the eye affliction may look directly at the person applying the drop without an awkward tilt of the head and the person applying the drop of therapeutic solution may do so by holding the drop dispenser relatively horizontal and applying the drop directly into the eye or conjunctival sac.

As those of skill in the art will recognize, the embodied drop dispensers and their associated cannula tips, allow for better drop size management by patients or users of the drop dispensers. These drop dispensers have the ability to maintain the desired drop size, and with a variety of cannula tips available the drop size from any given drop dispenser may be varied by a simple change in the cannula tips with varying sizes of apertures. Such drop dispensers and methods of use may help to overcome some of the issues related to variation in drop size due to the angle of administration. The drop dispensers and methods provided herein allow for easily repeatable administration, including optimal, repeatable angles of administration, thus reducing improper administration by patients and increasing administration procedure compliance while reducing waste and overuse.

One skilled in the art will readily realize that all ranges discussed can and do necessarily also describe all subranges therein for all purposes, and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While some embodiments have been illustrated and described, it should be understood that changes and modifications can be made therein in accordance with ordinary skill in the art without departing from the invention in its broader aspects as defined in the following claims.

What is claimed is:

1. A drop dispenser comprising:
   a first portion comprising a dispensing tip comprising an annular groove around an outer part of the dispensing tip and a nozzle comprising a through-opening;
   a second portion comprising a closed end; and
   a removable cannula tip comprising;
      an aperture; and
      an elastomeric annular ring distal to the aperture;
   wherein;
      the first portion is angularly disposed from the second portion;
      the dispensing tip is distal from the closed end; and
      the elastomeric annular ring is configured to seat in the annular groove of the dispensing tip.

2. The drop dispenser of claim 1, wherein the aperture comprises a rounded edge.

3. The drop dispenser of claim 1, wherein the removable cannula tip is curved.

4. The drop dispenser of claim 1, wherein the drop dispenser contains a therapeutic solution.

5. The drop dispenser of claim 4, wherein the therapeutic solution is an ophthalmic solution, an auditory solution, or other topical therapeutic solution, or an insulin solution.

6. The drop dispenser of claim 4, wherein the dispensing tip is positioned on the first portion such that when the first portion is held relatively horizontal and the second portion is angularly displaced to an upward angle, the therapeutic solution can easily reach the dispensing tip.

7. The drop dispenser of claim 1, wherein the removable cannula tip is capable of dispensing a droplet of a therapeutic solution having a volume of from about 1 to about 50 µL.

8. The drop dispenser of claim 1, wherein the removable cannula tip further comprises a unidirectional valve.

9. The drop dispenser of claim 1, wherein the second portion is narrower at an end proximal to the first portion than at the closed end.

10. The drop dispenser of claim 1, wherein the first portion is narrower at an end distal to the second portion than at an end proximal to the second portion.

11. The drop dispenser of claim 1, wherein the first portion and the second portion are cone-shaped, such that an overall shape of the drop dispenser is conical from the closed end to the dispensing tip, and further wherein the closed end is the widest end of the drop dispenser.

12. The drop dispenser of claim 1, wherein the angular disposition is from about 90° to about 180°.

13. The drop dispenser of claim 1, wherein the angular disposition is from about 135° to about 178°.

14. The drop dispenser of claim 1, wherein the drop dispenser is constructed of a polymeric material.

15. The drop dispenser of claim 1, wherein the drop dispenser further comprises a transparent or translucent window.

16. The drop dispenser of claim 15, wherein the window further comprises graduation marks.

17. The drop dispenser of claim 1, wherein the drop dispenser further comprises a sterile cannula tip dispenser comprising a cylinder having an open end, and a closed end distal to the open end, such that the sterile cannula tip dispenser is capable of dispensing one cannula tip at a time.

18. A method of using the drop dispenser of claim 1, comprising:

providing a subject in need of an eye treatment with an ophthalmic solution contained within the drop dispenser;

holding the drop dispenser in a dispensing position, such that a face of the subject remains substantially vertical, the first portion of the drop dispenser is substantially horizontal and the second portion of the drop dispenser is angularly disposed at an upward angle;

bringing the aperture of the removable cannula tip into close proximity with an eye; and squeezing the drop dispenser to expel a drop of ophthalmic solution from the drop dispenser, through the removable cannula tip, out of the aperture, and onto the eye.

19. The method of claim 18, wherein the eye comprises a conjunctival sac and the drop is expelled into the conjunctival sac.

* * * * *